United States Patent [19]

McRobbie

[11] 4,064,156
[45] Dec. 20, 1977

[54] METHANATION OF OVERSHIFTED FEED
[75] Inventor: Henry William McRobbie, Ossining, N.Y.
[73] Assignee: Union Carbide Corporation, New York, N.Y.
[21] Appl. No.: 765,060
[22] Filed: Feb. 2, 1977
[51] Int. Cl.² .......................... C10J 1/00; C07C 9/04
[52] U.S. Cl. .................. 260/449.6 M; 48/197 R; 48/202; 260/449 S
[58] Field of Search .................. 48/197 R, 202, 206, 48/215; 260/449 M, 449.6 M, 449 S

[56] References Cited
U.S. PATENT DOCUMENTS 3,922,148  11/1975  Child .................................. 48/197 R
4,005,996  2/1977   Hausberger et al. ............. 48/197 R Primary Examiner—Robert L. Lindsay, Jr.
Assistant Examiner—George C. Yeung
Attorney, Agent, or Firm—Alvin H. Fritschler

[57] ABSTRACT

A process for the production of methane from feed gas comprising $H_2$ and CO wherein prior to methanation of feed gas fractions in a series of at least two primary, fixed bed, adiabatic, catalytic reactors, the ratio of $H_2$ to CO in the feed gas is over-shifted to greater than about 4 to 1 and then the ratio of $H_2$ and carbon oxides in the over-shifted feed gas is adjusted by removing a predetermined amount of $CO_2$ from the feed gas in order to moderate the temperature rise in the first methanation reactor in conjunction with steam. In addition, after the effluent gas from each primary reactor is cooled, by controlling the ratio of adjusted feed gas fraction to cooled effluent gas from the preceding primary reactor, the temperature rise in each succeeding primary reactor is moderated.

21 Claims, 1 Drawing Figure

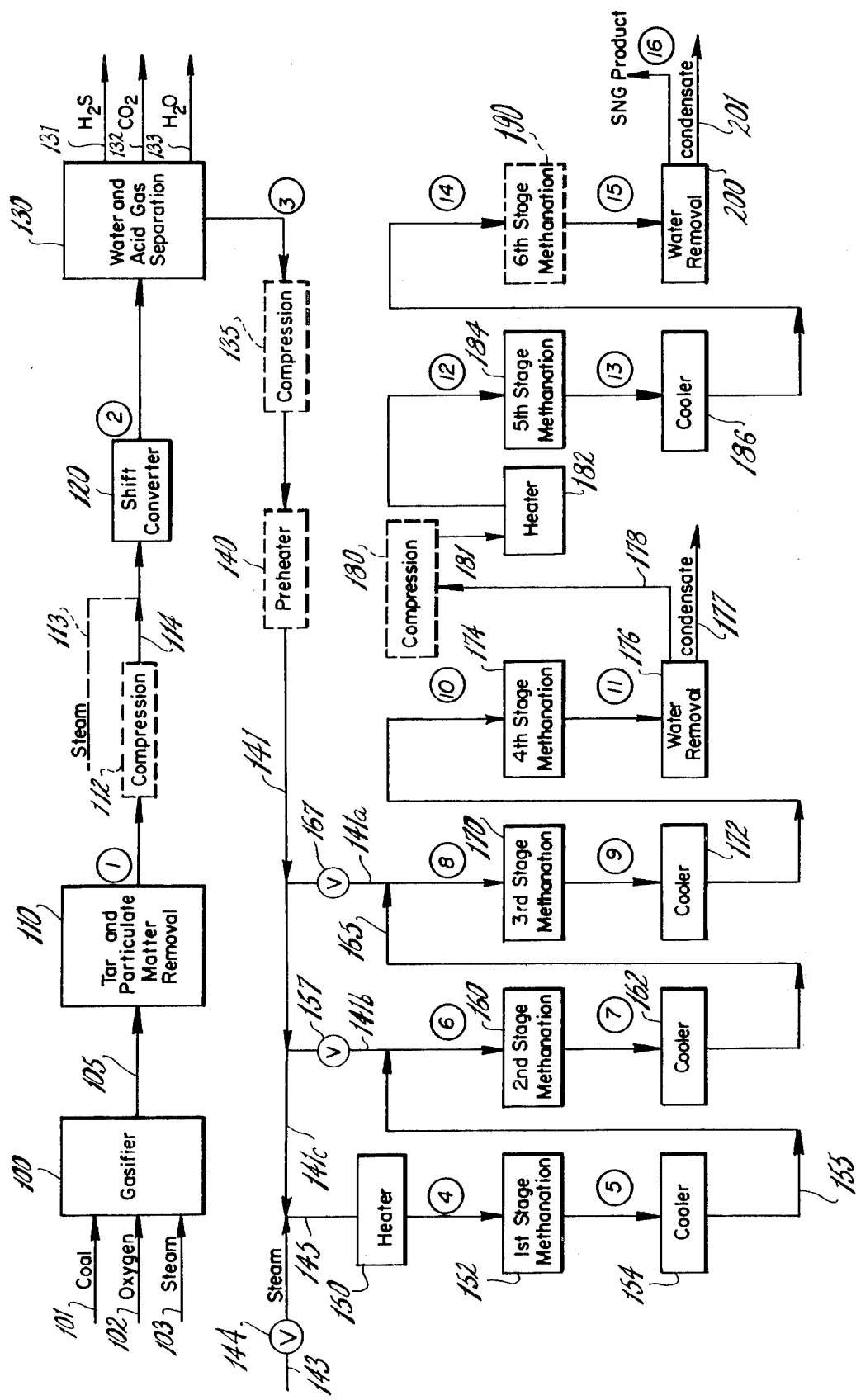

METHANATION OF OVERSHIFTED FEED

BACKGROUND OF THE INVENTION

1. Field of the Invention

This invention relates to the production of synthetic fuels and is particularly concerned with a process wherein a synthesis gas is methanated to produce a substitute pipeline gas having a heating value of about 900 to 1000 BTU per standard cubic foot from feed gas comprising carbon monoxide and hydrogen.

2. Description of the Prior Art

In the fixed bed catalytic methanation of gases containing carbon monoxide and hydrogen, the reaction between the carbon monoxide and hydrogen is very exothermic and, if not controlled within the reactor, can cause sintering of the catalyst, carbon deposition on the catalyst and/or thermal cracking of the product methane to carbon and hydrogen. Carbon formation through thermal cracking and/or carbon monoxide disproportionation in turn has a tendency to foul the catalyst bed. Furthermore, most nickel catalysts active for the methanation reactions will tend to deactivate at high temperatures. Consequently, it is of importance to limit the maximum temperature of the catalyst bed. Also, it is important that the gas enter at the lowest inlet temperature which will still give an acceptable initiation reaction rate and still prevent the formation of a carbonyl compound which can occur through the reaction of the carbon monoxide with the catalyst at temperatures below proper operating temperatures.

To overcome some of these problems caused by overheating or carbonyl formation, extensive recycle streams are used as diluent to absorb some of the exothermic heat evolved. Additional measures for avoiding too high temperatures in the reactor include cooling of the catalyst bed or of the reaction gases. For example, direct cold gas recycle and internal cooling of the reactor by heat transfer surfaces within the bed are recognized methods by which temperature controls may be effected. Local heating is difficult to avoid when using the latter and the building of internal exchange surfaces tends to be expensive. The hot gas recycle and direct cold gas recycle methods, on the other hand, require high recycle ratios. As a consequence, large pressure drops through the catalyst beds occur and the requirements for compressor power and strictor design specifications increase proportionately, hence increasing compression construction costs.

Catalytic methanation processes which employ a separate water gas shift conversion step and avoid using either a high recycle gas rate and/or very large heat removal between stages include U.S. Pat. Nos. 3,890,113 and 3,904,389.

SUMMARY OF THE INVENTION

It is an object of the invention to provide a process for the production of methane from feed gas comprising $H_2$ and CO wherein stoichiometric conversion of carbon oxides to methane is obtained and the exothermic reaction between CO and $H_2$ is controlled without the need of expensive internally cooled surfaces or high recycle ratios. Another object of the invention is to provide a process for the production of methane from feed gas comprising $H_2$ and CO wherein the catalyst damage by low or high temperatures is prevented with a minimum of investment and operating costs. Still another object is to provide a process for producing methane wherein the generation of a portion of the reaction heat is transferred out of the primary methanation reactors and into the shift converter. An additional object of this invention is to provide a methanation process which employs excess carbon dioxide in the feed gas as a diluent to absorb the exothermic heat evolved and moderate the outlet temperature developed in each primary adiabatic methanation reactor.

These and other objects of the invention are obtained by an improved process for the production of methane from mixtures of carbon oxides and hydrogen. In its broadest aspect, the invention relates to a process for the production of methane from a feed gas comprising $H_2$ and carbon oxides in a series of at least two primary, and at least one secondary, fixed-bed, adiabatic catalystic reaction zones each of which is separated by a cooling zone, wherein the effluent gas from each of the primary reaction zones is passed through a cooling zone and into the succeeding reaction zone, which process comprises: providing the feed gas, the molar ratio of $H_2$ to CO in the feed gas being greater than about 4 to 1; removing a portion of the $CO_2$ from the feed gas to adjust the ratio of $H_2$ and carbon oxides in the feed gas substantially according to the formula: $R_3 = x(R_2 - (\frac{1}{4})(R_o - 3R_1))$ wherein $x$ = a number between about 0.95 and about 1.07, $R_o$ = the fraction of hydrogen in the feed gas which is available for methanation of CO and $CO_2$, $R_1$ = the molar ratio of $CO/H_2$ in the feed gas, $R_2$ = moles $CO_2$ removed from the feed gas per moles $H_2$ in the feed gas; optionally preheating the adjusted feed gas to a temperature below the initiation temperature of the catalyst in the first primary reaction zone; splitting the feed gas into a plurality of fractions, preferably substantially equal to the number of primary reaction zones, introducing a first mixture comprised of steam and a first one of the fractions into the first primary reaction zone at a first inlet temperature above about the minimum initiation temperature of the catalyst therein, the amount of steam in the first mixture being sufficient to prevent both (1) carbon formation on the catalyst in each of the wet reaction zones and (2) overheating of the catalyst in the first primary reaction zone; adiabatically reacting the first mixture in the first primary reaction zone to produce an effluent gas, the steam CO, $CO_2$ and $H_2$ molar content in the first mixture being sufficient to moderate the temperature rise upon methanation from the first inlet temperature to a first outlet temperature below about the maximum operating temperature of the catalyst in the first primary reaction zone; introducing the effluent gas from the first and each succeeding primary reaction zone into a cooling zone wherein its temperature is regulated from the outlet temperature of the preceding primary reaction zone to a temperature sufficient to raise the inlet temperature of a second mixture and each succeeding mixture fed into the next primary reaction zone above about the minimum initiation temperature of the catalyst in the primary reaction zone to which the mixture is fed, the second mixture and each succeeding mixture comprised of one of the feed gas fractions and the cooled effluent gas from the primary reaction zone preceding the primary reaction zone to which the mixture is fed forming the second mixture and each of the succeeding mixtures, the molar ratio of each of the feed gas fractions to the cooling effluent gas in each of the mixtures being sufficient to moderate the temperature rise upon methanation of each mixture from the inlet temperature above about the minimum initiation temperature of the catalyst in the reaction zone to which the mixture is fed to an outlet temperature below the maximum operating temperature of the catalyst in the reaction zone to which the mixture is fed; forming the second mixture and each of the succeeding mixtures, the molar ratio of each of the fractions to the cooled effluent gas admixed therewith in each of the mixtures being sufficent to moderate the temperature rise upon its methanation from the inlet temperature above about the minimum initiation temperature of the catalyst in the reaction zone to which the mixture is fed to an outlet temperature below the maximum operating temperature of the catalyst in the reaction zone to which the mixture is fed; introducing the second mixture and each of the succeeding mixtures into the primary reaction zone succeeding the one whose effluent gas is employed to form the mixture; adiabatically reacting the second mixture and each of the succeeding mixtures to produce an effluent gas having the outlet temperature specified in the mixture forming step above; introducing the effluent gas from the last one of the primary reaction zones and each succeeding secondary wet reaction zone into a cooling zone wherein its temperature is regulated from an outlet temperature below about the maximum operating temperature of the catalyst in the preceding reaction zone to an inlet temperature above about the minimum initiation temperature of the catalyst in the succeeding reaction zone; adiabatically reacting the cooled effluent gas from the previous step in the succeeding secondary, wet reaction zone to produce a product gas rich in methane having a temperature below about the maximum operating temperature of the catalyst in the last of the secondary, wet reaction zones, the temperature rise in each of the secondary, wet reaction zones moderated by the steam, carbon oxides and hydrogen molar content in the cooled effluent gas from the previous step and condensing a substantial portion of the steam present in the product gas to water which is removed from the product gas. Further methanation of the product gas may be conveniently accomplished in one or more conventional secondary dry methanation zones as described subsequently.

By "primary" methanation reaction zone or reactor as used throughout the specification is meant a reactor which receives for methanation at least some synthesis gas which has not previously been methanated. By "secondary" methanation reaction zone or reactor is meant a reaction zone or reactor which receives for methanation a synthesis gas which has previously been subjected to methanation at least once.

By "overshifting" as used throughout the specification is meant subjecting a feed gas comprised of $H_2$ and CO to the water-gas shift reaction to produce a $H_2$ to CO ratio greater than the stoichiometric ratio of $H_2$ to CO required for conversion of CO to methane by the overall reaction.

By "dry" reaction zone as used throughout the specification is meant a reaction zone wherein methanation of a feed gas occurs in the substantial absence of water in the feed gas. By "wet" reaction zone is meant a reaction zone wherein methanation of a feed gas occurs in the presence of steam plus water vapor formed by the methanation of carbon oxides. Reactor and reaction zone are interchangeably used throughout the specification.

According to the process of this invention, the generation of heat is distributed more evenly through several reaction zones. In prior art processes, the heat load has generally been found in the first primary methanation reaction zone. However, according to applicant's invention, the heat load is transferred to the shift conversion zone and to the succeeding primary methanation reaction zone. This is accomplished by typically overshifting all of a feed gas comprised of $H_2$ and CO to a $H_2$/CO ratio greater than about 4 to 1 and then adjusting the ratio of $H_2$ and carbon oxides in the feed gas prior to its methanation. In some instances overshifting may be unnecessary since the feed gas may already have the desired $H_2$/CO ratio.

The process of this invention takes advantage of the fact that the heat evolved per mole of methane produced from the hydrogenation of carbon dioxide is considerably less than that from carbon monoxide conversion to methane. This is apparent from a comparison of the heats of reaction for the following reactions:

$$CO_2 + 4H_2 \rightleftarrows CH_4 + 2H_2O \qquad (1)$$

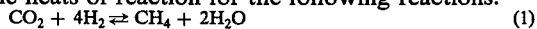

$$CO + 3H_2 \rightleftarrows CH_4 + H_2O \qquad (2)$$

As a result of overshifting and adjusting the ratio of $H_2$ and carbon oxides in the feed gas, the temperature rise in the first primary methanation reactor may be moderated. Temperature moderation in the first primary reactor is, however, primarily due to the presence of steam added thereto. Since the temperature rise is controlled by steam addition and $H_2$ and carbon oxides content in the feed gas in the first primary reactor, no recycle gas is required. Also, the higher partial pressure of hydrogen present in the overshifted feed gas is advantageous in suppressing the formation of elemental carbon in that portion of the catalyst bed situated in the vicinity of the feed gas inlet to the reactor.

Primary methanation in the process of this invention is carried out in a reaction system comprised of a series of two or more fixed-bed, adiabatic catalytic reactors. Heat is removed from the effluent gas of each primary reactor by passing the effluent gas through a cooling zone as it passes from one reactor to the succeeding reactor. The cooling zone may be a conventional heat exchanger, for example, a waste heat boiler.

The catalyst employed in the reactors may be any of the conventional higher temperature hydrogenation catalysts employed in methanation processes. These catalysts include, for example, the iron-transition group metals, iron, cobalt, nickel, or a platinum group metal, e.g. platinum, palladium, rubidium and ruthenium, in the elemental or combined state, e.g. their oxides, sulfides or their inorganic form. Mixtures of these materials or compounds can be used if desired. Catalytic amounts of a catalyst on suitable supports such as alumina may be employed. The preferred catalysts are nickel and iron oxide.

The most cost effective catalysts have generally been compositions containing nickel as the primary constituent. These catalysts may be used in conjunction with natural occurring supports such as kieselguhr, pumice, infusoral earth, asbestos, silica, alumina or the like.

Any number of catalytic zones or stages can be used, generally, the greater the concentration of carbon oxides to be methanated, the larger the number of stages.

Feed gas compositions subjected to the methanation process of the invention are comprised of carbon monoxide and hydrogen and may include, as well, other gases such as methane, ethane, nitrogen, carbon dioxide, argon, water vapor and the like. The feed gas is stripped of tar and particulate matter and subjected to shift conversion to obtain a hydrogen to CO ratio greater than about 4 to 1. The shift reaction does not ordinarily go to completion. The degree of completeness is limited by equilibrium, which is, in turn, dependent on the temperature and the concentration of the active species (CO, $H_2O$, $CO_2$ and $H_2$). By an appropriate choice of process conditions, a composition having the desired ratio of $H_2$ to CO may be obtained.

After shift conversion of the feed gas, it will generally contain excess $CO_2$ and steam and may also contain deleterious impurities such as sulfur compounds. Acid gases and water are hence removed. Sulfur compounds must be removed to residuals substantially under 4 ppm, and preferably less than 0.2 ppm to protect the catalysts employed in the methanation reactors which are poisoned by sulfur. After shift conversion of the feed gas, acid gases and water are removed.

In accordance with the process of this invention, the composition of the gases entering the reactors is adjusted to a content of steam, carbon oxides and hydrogen which when reacted or methanated will produce an amount of heat insufficient to raise the gas temperature above the maximum operating temperature of the catalyst employed. This maximum operating temperature varies from catalyst to catalyst and is known by those skilled in the art or easily determinable. In the case of nickel catalyst, for example, the maximum operating temperature is usually about 900° to 950° F.

Thus, in the first reactor or reaction zone of the system, a mixture of feed gas and steam is used with a steam, carbon oxides and hydrogen content sufficient to raise the mixture from an inlet gas temperature greater than the minimum initiation temperature of the catalyst in the first reactor to an outlet temperature no greater than the maximum operating temperature of the catalyst in the first reactor.

Additionally, according to the process of this invention a second mixture is formed by admixing the second feed gas fraction with the effluent gas from the first reactor in such proportions that when the steam, $H_2$ and carbon oxides content of the second mixture is methanated, the heat generated will be insufficient to raise the temperature of the second mixture above the maximum operating temperature of the catalyst in the second primary reaction zone.

After adiabatic reaction in the first primary reactor and cooling in a cooling zone, the first effluent gas is deficient in $H_2$ and CO. Hence, if the first effluent gas were to be reacted by itself in the second primary reactor, a temperature rise much lower than that in the first primary reactor would result. This would be due to the lower equilibrium temperature reached since the heat of reaction was removed in the first primary reactor. The second feed gas fraction is, of course, rich in $H_2$ and CO. Admixing the second feed gas fraction with the first effluent gas therefore enriches the $H_2$ and CO content of the first effluent gas.

Conversely, the second feed gas fraction is rich in $H_2$ and CO and if not regulated, adiabatic methanation of the second fraction by itself would result in a temperature rise in the second primary reactor that would exceed the maximum operating temperature of the catalyst situated therein. The cooled effluent gas from the first primary reactor contains large quantities of water vapor, i.e. the steam initially added to the first primary reactor and steam generated in the methanation reaction therein as well as methane. The water vapor and methane in the cooled effluent gas soaks up heat evolved during methanation of the second feed gas fraction and hence moderates the temperature rise of the reaction of the mixture of cooled effluent gas and second feed gas fraction. The ratio of second feed gas fraction that should be admixed with the cooled first effluent gas should be sufficient to regulate the temperature rise to a second effluent gas temperature below the maximum operating temperature of the catalyst employed in the second primary reactor.

The inlet temperature for each of the primary reactors will usually be similar and at or above the initiation temperature of the catalyst in the reactor. Carbon formation is prevented in each primary reactor by adding steam to the first feed gas fraction passed into the first primary reactor in an amount sufficient to prevent carbon formation therein and in each subsequent primary reactor. The steam added to the first primary reactor plus the steam generated in each subsequent wet methanation reactor is passed, along with the effluent gas into the succeeding wet methanation reactor. The operating limits for the inlet and outlet temperatures for each primary reactor will vary primarily with the catalyst utilized therein. In the case of nickel catalyst, for instance, inlet temperatures will fall in the range of about 550° F to about 650° F and outlet temperatures will vary from about 850° F to about 950° F.

BRIEF DESCRIPTION OF THE DRAWING

The invention will be illustrated in further detail by reference to the sole FIGURE which is a schematic flow sheet illustrating a preferred embodiment of the disclosed process.

DESCRIPTION OF THE PREFERRED EMBODIMENTS

According to the present invention, there is essentially provided a process for the production of a substitute pipeline gas from a synthesis gas. The process is carried out in a manner which avoids potential carbon formation and deposition on catalysts employed in the methanation stages. Shown in the FIGURE are gasifier 100, tar and particulate matter removal zone 110, shift conversion zone 120, water and acid gas separation zone 130, preheater 150, three primary methanation zones 152, 160 and 170, water removal zone 176, heater 182, secondary methanation zones 174 and 184 and water removal zone 200.

The FIGURE is a schematic flow diagram illustrating a process in which a raw synthesis gas produced by gasification of coal is methanated in the presence of a catalyst. It will be understood that the invention is not restricted to the methanation of synthesis gases produced from coal and is equally applicable for the upgrading of synthesis gas and similar mixtures of carbon oxides and hydrogen derived from shale oil, heavy crude oils, petroleum coke, residual petroleum fractions, napththas and the like.

In gasification reactor 100, synthesis gas comprising principally hydrogen, carbon monoxide, carbon dioxide, water vapor, methane, and one or more members of the group consisting of nitrogen, argon, carbonyl sulfide, and hydrogen sulfide, as well as entrained particulate carbon is produced by the reaction of a hydrocarbonaceous fuel by partial oxidation with oxygen and/or steam at temperatures between about 1200° F and about 2500° F and at pressures between about 30 psi to about 2000 psi or greater.

The gasification reactor may represent a conventional Texaco Synthesis Gas Generator or other reactor employed in known gasification processes. Typical of these processes are the HYGAS Process proposed by the Institute of Gas Technology, the CSC Process of Consolidated Coal Co., the Bi-Gas Process of Bituminous Coal Research, Inc., the Synthane Process of the Bureau of Mines and the COGAS Process of FMC Corporation. Older processes which have been employed commercially for the manufacture of low BTU gas include the Koppers-Totzek process of the Koppers Company and the Lurgi Process of the Lurgi Gesellschaft of Frankfurt, Germany.

The effluent gas from the gasification reactor may have the following gas composition in mole precent:

TABLE I

| RAW SYNTHESIS GAS COMPOSITION | |
|---|---|
| Component | Mole Percent (Dry Basis) |
| $H_2$ | 20–59 |
| CO | 10–70 |
| $CO_2$ | 5–40 |
| $H_2S$ | 0–2.0 |
| $CH_4$ | 0–25 |
| COS | 0–0.1 |
| $N_2$,Ar | 0–2 |

The effluent gas stream 105 from gasifier reactor 100 is passed into scrubbing zone 110 to remove tar, particulate carbon and any other entrained solids. Well known scrubbing techniques may be employed to remove tar and particulate material such as scrubbing effluent gas stream 105 with a scrubbing fluid comprising oil, water or both at high pressures and temperatures. Excessive cooling of the effluent gas stream 105 should be avoided so as to retain water in the gas stream ①. The circled numbers in the in the FIGURE are used to designate both the gas stream composition at that point in the process as well as the line conveying the stream.

When required, additional scrubbing may be provided to supplement the previously mentioned gas scrubbing. For example, the gas stream may be quenched in hydrocarbon oil or washed with a liquid hydrocarbon fuel by means of a scrubbing nozzle or venturi scrubber, such as described in Perry's Chemical Engineers' Handbook Fourth Edition, McGraw Hill 1963, Pages 18–56. The process gas stream leaves the top of the scrubbing tower substantially free of particulate material and at a temperature in the range of about 400° F to 650° F.

The scrubbed effluent gas stream ① is optionally pressurized in compression zone 112 to at least 100 psi, said pressure being sufficient to transport gas through the shift converter and successive stages allowing for pressure drops. The pressurized effluent gas stream ① passes out of zone 112 through line 114. Stream is optionally added to line 114 via line 113 prior to passing the gaseous effluent stream ① into shift conversion zone 120 since steam is required for the shift conversion reaction. Steam may also be supplied in sufficient quantities in the prior scrubbing zone.

A portion of the carbon monoxide in the process gas is reacted with steam to produce carbon dioxide and additional hydrogen by means of the water-gas shift reaction. This reaction is equilibrium limited and does not normally go to completion. Equilibrium is dependent on the temperature and the concentration of the active species (CO, $H_2O$, $CO_2$ and $H_2$). By an appropriate choice of process conditions, it is possible to arrive at a composition wherein the ratio of $H_2$ to CO is greater than 4 to 1.

To facilitate the water-gas shift reaction, catalysts such as copper or zinc oxide and ferric oxide promoted by chromic oxide have been used. More recently, it has been disclosed that alkali metal compounds are effectively water-gas shift reaction catalysts at temperatures of from about 400° F and are less affected by sulfur compounds than many of the earlier materials. A sulfur resistant shift catalyst is generally required.

The water-gas shift reaction generates excess hydrogen from hydrogen poor synthesis gas. In fact, according to the process of this invention, more hydrogen than is necessary to react with the carbon monoxide in the synthesis gas to form methane is produced in the water gas shift converter. Also, excess carbon dioxide is produced. It is desirable to remove part of the excess carbon dioxide prior to methanation because if left in, an additional acid gas removal step would be required subsequently in the process or the product gases would contain high $CO_2$ content which is undesirable.

From shift conversion zone 120, the effluent gas stream passes through line ② into a water and acid gas separation zone 130. The shifted synthesis gas stream is cooled to a suitable temperature for operation of a selective acid gas removal. For example, the shifted gas stream may be passed through an in-line wasteheat boiler (not shown) and cooled to a temperature in the range of about 80° F to 200° F by indirect heat exchange with water, thereby producing steam which may be used elsewhere in the process.

$CO_2$, $H_2O$ and $H_2S$ may be removed from the process gas stream ② in water and acid-gas separation zone 130 via lines 132, 133 and 131 respectively. For example, the gas cooled to 100° F may be physically or chemically absorbed with alkaline absorbents (solvents), such as n-methyl pyrrolidone, triethanolamine, propylene carbonate, or alternatively with methylalcohol, or promoted alkali carbonates such as hot potassium carbonate. Methane should be substantially insoluble in the solvent selected.

Hydrogen sulfide and other sulfur bearing gases, together with part of the carbon dioxide, are absorbed selectively or non-selectively by the solvent.

Most the $CO_2$ absorbed in the solvent can be released by simple flashing, the rest being removed by stripping. This may be done most economically with impure nitrogen that is available free of cost when an air-separation unit is used to provide oxygen for the gasifier. The regenerated solvent is then recycled to the absorption column for reuse. When necessary, final cleanup may be accomplished by passing the process gas through iron oxide, zinc oxide or activated carbon to remove residual traces of $H_2S$ or organic sulfide.

Similarly, $H_2S$ and COS- containing solvents may be regenerated by further flashing and stripping with nitrogen. If the sulfur compounds are present in quantities higher than 50–100 ppm, a selective process for extracting sulfur is preferable so as to make possible the recovery of sulfur in a stream of sufficient concentration to permit conversion to sulfur or sulfuric acid in a suitable process. For example, the Claus process may be used to produce elemental sulfur from $H_2S$ as described in Kirk-Othmer Encyclopedia of Chemical Technology, Second Edition, Volume 19, John Wiley, 1969, page 352. If the sulfur compounds are present in quantities less than 50 ppm, it is usually more economic to absorb the sulfur on zinc oxide or similar absorbents which can be disposed of by batch removal from the system. A combination of sulfur extraction and final cleanup by absorption on zinc oxide may also be used. This part of the technology is well known and selection of a particular route is governed mainly by economics.

The amount of carbon dioxide removed from the shifted synthesis gas ② in separation zone 130 via line 132 is determined according to the formula:

$$R_3 = x(R_2 - (\tfrac{1}{4})(R_o - 3R_1))$$

wherein $x$, $R_o$, $R_1$, $R_2$ and $R_3$ are as defined previously herein. Hydrogen may not be 100 percent available for methanation of carbon oxides where it has been consumed in reformed hydrocarbons heavier than methane such as ethane, propane and the like and in the hydrogenation of any olefins present in the feed gas. The factor $x$ expresses the allowable variation by which the desired stoichiometric ratio of $H_2$ to carbon oxides can be varied.

Synthesis gas stream ③ may optionally be pressurized in compression zone 135 before being optionally preheated in preheater 140 to a temperature such that after portions of the synthesis gas ③ are mixed with cooled effluent gas from the first or second primary reaction zones, the mixture of first or second cooled effluent gas and feed gas portions will have a temperature high enough to initiate reaction zones 160 and 170, respectively. Generally, synthesis stream ③ is preheated to a temperature of about 200° F, to about 450° F, preferably to a temperature of about 400° F to about 450° F.

Preheated feed gas ③ is split into a number of fractions depending on the number of primary reaction zones desired. In the embodiment illustrated in the Figure, three primary reaction zones for methanation are shown and hence the feed gas ③ is split into fractions 141a, 141b, and 141c. Each fraction is apportioned to control temperature rise in each primary methanation reaction zone. Steam is admixed with feed gas fraction 141c via line 143 and valve 144. The resultant mixture is preheated and fed through line 145 into reaction zone 152. The ratio of steam to synthesis gas fraction 141c should be sufficient to prevent the development of excess heat in methanation reaction zone 152. Steam is the primary temperature moderator in reaction zone 152 although the $H_2$ and carbon oxides content of synthesis gas fraction 141c also contributes to temperature moderation in reaction zone 152. Methane is formed by the reaction of carbon oxides contained in the desulfurized synthesis gas fraction 141c with hydrogen in reaction zone 152.

Methanation is carried out in multiple stages without requiring recycle, provisions being made for cooling the effluent gas between successive stages to recover the exothermic heat which is liberated during the methanation reaction. This generally involves a series of separate reactors with heat exchangers or other heat recovery units interposed between adjacent reaction vessels. The reactors used are typically fixed bed units.

In the system shown in the FIGURE, four methanation reactors of fixed bed type designated by reference numerals 152, 160, 170 and 174 and three heat exchangers or similar heat recovery units designated by reference numerals 154, 162 and 171 are provided. The reactors shown are of the down type in which the gas moves downwardly through catalyst particles supported on trays or similar internal supporting elements but fixed bed units of other types can also be used.

Steam at a temperature between about 330° F and about 800° F is admixed with split synthesis gas fraction 141c. The mixture is preheated in heat exchanger 150 to provide an inlet temperature sufficient to initiate the methanation reaction and prevent carbonyl formation in the first primary reaction zone 152. The inlet temperature for reaction zone 152 should be between about 500° F and 700° F, preferably between about 550° F and 650° F.

Among the constituents of the synthesis gas, CO and $CH_4$ are precursors of carbon. Carbon formation can be prevented by lowering the partial pressures of CO and $CH_4$ below those predicted by their respective carbon equilibria. Steam is employed to reduce partial pressures of CO and $CH_4$ in the synthesis gas feed and hence prevent carbon deposition in each methanation reaction zone. The presence of steam also influences both the methanation and carbon monoxide shift equilibria as water is a product of the first. The quantity of steam necessary to suppress carbon formation in subsequent catalytic methanation reactors and to limit the temperature rise in the first primary reaction zone 152 is added to synthesis gas fraction 141c.

As previously described, the mixture is then further preheated in heat exchanger 150 to a level just above the initiation temperature of the catalyst contained in the first methanation reaction zone 152. Suitable catalysts for the first methanation zone include any conventional methanation catalysts capable of operating at temperatures between about 500° F and about 950° F.

In the first and subsequent two primary methanation reaction zones shown, the feed mixture enters at a temperature between about 500° F and about 700° F, preferably between about 550° F and about 650° F. As the feed mixture passes through the catalyst mass in each of the three primary methanation reactors, temperatures rise rapidly and approach those calculated for conditions of thermodynamic equilibrium achieved under adiabatic reaction conditions. The effluent gas temperatures from the first three methanation reactors are between about 850° F and 950° F so as to obtain maximum conversion while preventing thermal cracking of the methane formed.

Following reaction in each of the three primary methanation reactors, the effluent gases passing through lines ⑤, ⑦ and ⑨, respectively, are cooled to a temperature above or equal to the initial inlet temperature of the succeeding stage in cooling units 154, 162 and 172, respectively. In each cooling unit, the gas is passed in indirect heat exchange with water or other cooling fluid and steam or other hot fluid is recovered.

Cooled first stage effluent gas exiting from cooler 154 via line 155 is admixed with a second feed gas fraction metered through valve 157 and conveyed by line ⑥. The cooling of reactor 152 effluent in cooler 154 is regulated so that the total feed mixture from lines 155 and 141b is at an inlet temperature sufficient to initiate reaction in reactor 160, the second primary stage. The molar ratio of the second feed gas fraction to cooled first stage effluent gas in the mixture should be sufficient to moderate the temperature rise upon methanation of the mixture in reactor 160 so that an outlet temperature below the maximum operating temperature of the catalyst in reactor 160 is achieved.

The flow through the remaining primary methanation stage is similar. Cooled second stage effluent gas exiting from cooler 162 via line 165 is admixed with a third feed gas fraction metered through valve 167 and conveyed by line 141a. The cooling of reactor 160 effluent in cooler 162 is regulated so that the total feed mixture from lines 165 and 141a is at an inlet temperature sufficient to initiate reaction in reactor 170, the third primary stage. The molar ratio of the third feed gas fraction to cooled second stage effluent gas in the mixture should be sufficient to moderate the temperature rise upon methanation of the mixture in reactor 170 so that an outlet temperature below the maximum operating temperature of the catalyst in reactor 170 is achieved.

Cooled third stage effluent gas exits from cooler 172 (which operates in a manner similar to that of coolers 154 and 162) and passes directly into the fourth stage methanation reactor 174 through line ⑩. The temperature of the cooled effluent gas from the third and last primary reactor corresponds to the inlet temperature for the fourth reactor 174. This inlet temperature is sufficient to initiate reaction in the fourth reactor 174. The fourth methanation reactor 174 is a wet reaction zone and the first secondary reaction zone. Reaction zone 174 substantially completes the bulk of the methanation of the feed gas and its outlet temperature is generally substantially below that of the primary reaction zones.

The equilibrium composition of the effluent gas from the third primary reactor 170, when reacted in the fourth reactor 174 at an inlet temperature above the minimum initiation temperature of the catalyst situated in the fourth reactor, will not provide as large a temperature rise as occurred in primary reactors 152, 160 and 170. The high content of reactive constituents, i.e. the $H_2$ and CO, formerly in the feed gas, has been substantially depleted. Certainly, there is much less $H_2$ and CO content in the effluent gas from the primary reactor 170 than existed in the feed gas mixtures passing through lines ④, ⑥ and ⑧ to reactors 152, 160 and 170, respectively.

Although only three primary methanation reactors are illustrated in the FIGURE, two or more than three primary methanation reactors may be employed in the process of this invention. The advantage of using more than two primary methanation reactors is that the ratio of steam to total synthesis gas decreases as the number of primary methanation reactors is increased. This results in all of the moderating steam being introduced into the first primary methanation reactor, with the fresh feed gas fraction to each successive primary methanation reactor being regulated to hold the maximum reaction temperature of the subsequent reactor below the maximum operating temperature of the catalyst situated therein. The amount of steam introduced into the first primary methanation reactor relative to the total shifted feed will then depend on the total number of primary methanation reactors to be employed.

Effluent gas from the fourth methanation reactor 174 is passed via line ⑪ into water removal zone 176. Condensate water in the effluent gas is separated via line 177 to provide a product gas of enhanced heating value which can be converted to a final gas product of high heating value in the order of 900-1000 BTU/SCF by further treatment in dry methanation stages.

The substantially dry gas stream 178 is then optionally compressed in compressor 180 to a pressure above the end product pressure allowing for pressure drops during the subsequent stages, preheated in heat exchange unit 182 to a temperature above the initiation temperature of the catalyst in the subsequent methanation stage, and introduced via line ⑫ at a temperature of about 550° F into a secondary methanation zone. Three secondary methanation zones 174, 184 and 190 are illustrated in the FIGURE. The two dry methanation stages 184 and 190 shown operate at successively lower outlet temperatures and the stage 184 is followed by cooling unit 186 which lowers the temperature of the effluent gas stream ⑭ to an inlet temperature for methanation zone 190 substantially equal to or above the initiation temperature of the catalyst contained therein. By operating the two dry secondary methanation stages 184 and 190 at successively lower outlet temperatures, the methane content of the effluent gas may be increased substantially as the gas passes from one methanation stage to the next.

Following the last stage 190 in the process, most of the moisture is removed via condensate line 201 and water removal zone 200 to provide a product gas having a B.T.U. content similar to that of natural gas.

Although the operating pressure has not been specified, it is usually advantageous to operate at moderate pressure. Methanation is enhanced by high pressure, and the volume of the gases decreases as methanation proceeds. Therefore, pressure is a variable which is subject to economic optimization. Costs of compression and compression equipment increase with increasing pressure. These costs maybe outweighted, however, by improved product yield and by savings on vessels and piping of smaller size made possible by the use of higher pressure.

The following example is intended to illustrate the invention without limiting it in any manner.

EXAMPLE

A typical embodiment of the process of this invention is set forth below in Table II illustrated by a material balance, obtained by carrying out the process shown in the FIGURE. The block diagram of the FIGURE represents the main process steps. The material balance specifically applies to the process steps as numbered on the FIGURE.

The material balance computations are based on production of 100 pound moles per hour of a high heating value substitute natural gas from a coal gasifier effluent, corresponding in composition to that from a Koppers-Totzek type gasifier. Temperature rise in each primary reactor is restricted to the range of 500° F to 950° F.

The requisite quantity of steam is injected with the feed gas fraction 141c into the first primary methanation stage 152 via line 145 to hold the temperature rise in that stage to the maximum allowable. Cooled product gas from the first and each succeeding primary stage is mixed with the quantity of fresh feed fraction which will produce the same maximum temperature rise. The inlet temperature of 550° F and outlet temperature of 900° F have been found experimentally to provide a close approach to equilibrium and long catalyst life with such conventional methanation catalysts as Girdler G-65, a nickel catalyst, under the conditions indicated in Table II below:

TABLE II

MATERIAL BALANCE PRODUCTION OF SNG

| Stream No. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Component | | | | | | | | | | | | | | | | |
| Inerts | 0.6 | 0.4 | 0.6 | 0.2 | 0.2 | 0.2 | 0.2 | 0.3 | 0.3 | 0.4 | 0.4 | 2.1 | 2.3 | 2.3 | 2.3 | 2.6 |
| $H_2$ | 32.4 | 54.1 | 77.6 | 18.7 | 8.1 | 20.8 | 9.2 | 23.2 | 9.8 | 9.8 | 3.6 | 20.9 | 3.5 | 3.5 | 0.9 | 1.0 |
| $H_2O$ | * | * | * | 75.9 | 86.1 | 70.4 | 81.4 | 64.7 | 77.0 | 77.0 | 82.8 | 0.3 | 10.0 | 10.0 | 11.5 | * |
| CO | 56.8 | 6.5 | 9.3 | 2.2 | <0.1 | 1.7 | <0.1 | 1.9 | <0.1 | <0.1 | <0.1 | <0.1 | <0.1 | <0.1 | <0.1 | <0.1 |
| $CO_2$ | 9.9 | 38.8 | 12.4 | 3.0 | 2.0 | 3.9 | 2.3 | 4.3 | 2.4 | 2.4 | 0.9 | 5.2 | 0.9 | 0.9 | 0.2 | 0.2 |
| $CH_4$ | 0.1 | <0.1 | 0.1 | <0.1 | 3.6 | 3.0 | 6.9 | 5.5 | 10.4 | 10.4 | 12.3 | 71.5 | 83.2 | 83.2 | 85.1 | 96.1 |
| $H_2S$ | 0.2 | 0.1 | 0.0 | 0.0 | 0.0 | 0.0 | 0.0 | 0.0 | 0.0 | 0.0 | 0.0 | 0.0 | 0.0 | 0.0 | 0.0 | 0.0 |
| Flow Rate (pound moles/hr.) | 430 | 860 | 442 | 612 | 571 | 698 | 649 | 817 | 751 | 751 | 727 | 126 | 115 | 115 | 113 | 100 |
| Temperature (° F) | — | — | — | 550 | 900 | 550 | 900 | 550 | 900 | 550 | 689 | 550 | 850 | 550 | 596 | — |
| Pressure (psig.) | — | — | — | — | 385 | — | 375 | — | 365 | — | 355 | — | 1020 | — | 1010 | — |
| Heating Value (Btu/cf-gross)* | — | — | — | — | — | — | — | — | — | — | — | — | 947 | 947 | 979 | 979 |

*Dry Basis

While a particular embodiment of the present invention has been described, it will be understood, of course, that this invention is not limited thereto since many modifications may be made and it is, therefore, contemplated to cover by the appended claims any and all such modifications as may fall within the true spirit and scope of this invention.

What is claimed is:

1. A process for the production of methane from a feed gas comprised of hydrogen and carbon oxides in a series of at least two primary and at least one secondary wet, fixed bed, adiabatic, catalytic reaction zones each of which is separated by a cooling zone except the last zone wherein the effluent gas from each of the primary reaction zones is passed through a cooling zone and into the succeeding reaction zone, which process comprises:
   a. providing said feed gas, the molar ratio of $H_2$ to CO in said feed gas being greater than about 4 to 1;
   b. removing a portion of said $CO_2$ from said feed gas to adjust the ratio of $H_2$ and carbon oxides therein substantially according to the formula:

$$R_3 = x(R_2 - (\tfrac{1}{3})(R_0 - 3R_1))$$

wherein, $x$ = a number between about 0.95 and about 1.07, $R_0$ = the fraction of hydrogen in said feed gas which is available for methanation of CO and $CO_2$, $R_1$ = the molar ratio of $CO/H_2$ in said feed gas, $R_2$ = the molar ratio of $CO_2/H_2$ in said feed gas, and $R_3$ = the moles $CO_2$ removed from said feed gas per moles $H_2$ in said feed gas;
   c. splitting said feed gas into a plurality of fractions;
   d. introducing a first mixture comprised of steam and a first one of said fractions into said first primary reaction zone at a first inlet temperature above about the minimum initiation temperature of the catalyst therein, the amount of steam in said first mixture being sufficient to prevent both (1) carbon formation on the catalyst in each of said reaction zones and (2) overheating of said catalyst in said first primary reaction zone;
   e. adiabatically reacting said first mixture in said first primary reaction zone to produce an effluent gas the steam, carbon oxides and hydrogen molar content in said first mixture being sufficient to moderate the temperature rise upon methanation from said first inlet temperature to a first outlet temperature below about the maximum operating temperature of said catalyst in said first primary reaction zone;
   f. introducing the effluent gas from said first and each succeeding primary reaction zone into a cooling zone wherein its temperature is regulated from the outlet temperature of the preceding primary reaction zone to a temperature sufficient to raise the inlet temperature of a second mixture and each succeeding mixture fed into the next primary reaction zone above about the minimum initiation temperature of the catalyst in the primary reaction zone to which the mixture is fed, said second mixture and each succeeding mixture comprised of one of said fractions and the cooled effluent gas from the primary reaction zone preceding the one to which the mixture is fed;
   g. forming said second mixture and each of said succeeding mixtures, the molar ratio of each of said fractions to the cooled effluent gas in each of said mixtures being sufficient to moderate the temperature rise upon its methanation from said inlet temperature above about the minimum initiation temperature to an outlet temperature below the maximum operating temperature of the catalyst in the reaction zone to which the mixture is fed;
   h. introducing said second mixture and each of said succeeding mixtures into the primary reaction zone succeeding the one whose effluent gas is employed to form the mixture;
   i. adiabatically reacting said second mixture and each of said succeeding mixtures to produce an effluent gas having said outlet temperature specified in step (g);
   j. introducing the effluent gas from the last of said primary reaction zones and each succeeding secondary wet reaction zone into a cooling zone wherein its temperature is regulated from an outlet temperature below about the maximum operating temperature of the catalyst in the preceding reaction zone to an inlet temperature above about the minimum initiation temperature of the catalyst in the succeeding reaction zone;
   k. adiabatically reacting the cooled effluent gas from step (j) in the succeeding secondary, wet reaction zone to produce a product gas rich in methane having a temperature below about the maximum operating temperature of the catalyst in the last of said secondary, wet reaction zones, the temperature rise in each of said secondary, wet reaction zones moderated by the steam, carbon oxides and hydrogen molar content in the cooled effluent gas from step (j); and
   m. condensing a substantial portion of the steam present in said product gas to water which is removed from said product gas.

2. A process as defined in claim 1 wherein in step (a), said molar ratio is for said feed gas is provided by subjecting said feed gas to water gas shift reaction.

3. A process as defined in claim 1 wherein after step (b) and before step (c), said adjusted feed gas is preheated to a temperature below about the initiation temperature of the catalyst in the first primary reaction zone.

4. A process as defined in claim 1 further including after step (m):
n. subjecting said product gas to at least one secondary, dry fixed bed, adiabatic, catalytic reaction zone to convert residual $H_2$ and CO to methane and steam; and
o. condensing a substantial portion of said steam in said product gas from step (n) to water which is removed therefrom to provide a substitute natural gas.

5. A process as defined in claim 1 wherein the catalyst in each reaction zone is a nickel catalyst.

6. A process as defined in claim 1 wherein said first inlet temperature is between about 500° F and about 700° F and said first outlet temperature is between about 850° F and about 950° F.

7. A process as defined in claim 1 wherein in step (g), inlet temperature is between about 500° F and 700° F and said outlet temperature is between about 850° F and about 950° F.

8. A process as defined in claim 1 wherein in step (j), said inlet temperature is between about 500° F and about 700° F.

9. A process as defined in claim 1 wherein said feed gas is provided by the gasification of a hydrocarbonaceous feedstock which gaseous effluent is purified to remove the impurities therefrom comprising the residual carbon and sulfur impurities.

10. A process for the production of methane from a feed gas comprised of hydrogen and carbon oxides in a series of at least two primary and at least one secondary wet, fixed bed, adiabatic, catalytic reaction zones each of which is separated by a cooling zone except the last zone wherein the effluent gas from each of the primary reaction zones is passed through a cooling zone and into the succeeding reaction zone, which process comprises:
a. providing said feed gas, the molar ratio of $H_2$ to CO in said feed gas being greater than about 4 to 1;
b. removing a portion of said $CO_2$ from said feed gas to adjust the ratio of $H_2$ and carbon oxides therein substantially according to the formula:

$$R_3 = x(R_2 - (\tfrac{1}{4})(R_0 - 3R_1))$$

wherein $x$ = a number between about 0.95 and about 1.07, $R_0$ = the fraction of hydrogen in said feed gas which is available for methanation of CO and $CO_2$, $R_1$ = the molar ratio of $CO/H_2$ in said feed gas, $R_2$ = the molar ratio of $CO_2/H_2$ in said feed gas, and $R_3$ = the moles $CO_2$ removed from said feed gas per moles $H_2$ in said feed gas;
c. splitting said feed gas into a plurality of fractions;
d. admixing steam with a first one of said fractions to form a first mixture having a temperature above the dew point of the steam in the mixture, the amount of said steam being sufficient to prevent both (1) carbon formation on the catalyst in each of said reaction zones and (2) overheating of the catalyst in the first primary reaction zone;
e. preheating said first mixture to a first inlet temperature above about the minimum initiation temperature of the catalyst in the first primary reaction zone;
f. adiabatically reacting said first mixture in said first primary reaction zone to produce an effluent gas, the steam, carbon oxides and hydrogen molar content in said first mixture being sufficient to moderate the temperature rise upon methanation from said first inlet temperature to a first output temperature below about the maximum operating temperature of said catalyst in said first primary reaction zone;
g. introducing the effluent gas from said first and each succeeding primary reaction zone into a cooling zone wherein its temperature is regulated from the outlet temperature of the preceding primary reaction zone to a temperature sufficient to raise the inlet temperature of a second mixture and each succeeding mixture fed into the next primary reaction zone above about the minimum initiation temperature of the catalyst in the primary reaction zone to which the mixture is fed, said second mixture and each succeeding mixture comprised of one of said fractions and the cooled effluent gas from the primary reaction zone preceding the one to which the mixture is fed;
h. forming said second mixture and each of said succeeding mixtures, the molar ratio of each of said fractions to the cooled effluent gas in each of said mixtures being sufficient to moderate the temperature rise upon its methanation from said inlet temperature above about the minimum initiation temperature to an outlet temperature below the maximum operating temperature of the catalyst in the reaction zone to which the mixture is fed;
i. introducing said second mixture and each of said succeeding mixtures into the primary reaction zone succeeding the one whose effluent gas is employed to form the mixture;
j. adiabatically reacting said second mixture and each of said succeeding mixtures to produce an effluent gas having said outlet temperature specified in step (g);
k. introducing the effluent gas from the last of said primary reaction zones and each succeeding secondary wet reaction zone into a cooling zone wherein its temperature is regulated from an outlet temperature below about the maximum operating temperature of the catalyst in the preceding reaction zone to an inlet temperature above about the minimum initiation temperature of the catalyst in the succeeding reaction zone;
m. adiabatically reacting the cooled effluent gas from step (j) in the succeeding secondary, wet reaction zone to produce a product gas rich in methane having a temperature below about the maximum operating tempera- of the catalyst in the last of said secondary, wet reaction zones the temperature rise in each of said secondary, wet reaction zones moderated by the steam, carbon oxides and hydrogen molar content in the cooled effluent gas from step (j); and
n. condensing a substantial portion of the steam present in said product gas to water which is removed from said product gas.

11. A process as defined in claim 10 wherein in step (a), said molar ratio is for said feed gas is provided by subjecting said feed gas to water gas shift reaction.

12. A process as defined in claim 10 wherein after step (b) and before step (c), said adjusted feed gas is preheated to a temperature below about the initiation temperature of the catalyst in the first primary reaction zone.

13. A process as defined in claim 10 further including after step (n):
   o. subjecting said produce gas to at least one secondary, dry, fixed bed adiabatic, catalytic reaction zone to convert residual $H_2$ and CO to methane and steam; and
   p. condensing a substantial portion of said steam in said product gas from step (o) to water which is removed therefrom the provide a substitute natural gas.

14. A process as defined in claim 10 wherein the catalyst in each reaction zone is a nickel catalyst.

15. A process as defined in claim 10 wherein said first inlet temperature is between about 500° F and about 700° F and said first outlet temperature is between about 850° F and about 950° F.

16. A process as defined in claim 10 wherein in step (h) said inlet temperature is between about 500° F and 700° F and said outlet temperature is between about 850° F and about 950° F.

17. A process as defined in claim 10 wherein in step (k), said inlet temperature is between about 500° F and about 700° F.

18. A process as defined in claim 10 wherein said feed gas is provided from the gasification of a hydrocarbonaceous feed stock which gaseous effluent is purified to remove the impurities therefrom comprising the residual carbon and sulfur impurities.

19. A process as defined in claim 10 wherein in step (e), said adjusted feed gas is preheated to a temperature between about 200° F and about 450° F.

20. A process as defined in claim 10 wherein in step (e), said adjusted feed gas is preheated to a temperature between about 400° F and 450° F.

21. A process as defined in claim 10 wherein in step (d), said steam admixed with said first fraction is at a temperature between about 330° F and about 800° F.

* * * * *